United States Patent [19]
> Yang et al.

[11] Patent Number: 5,969,000
[45] Date of Patent: Oct. 19, 1999

[54] DENTAL RESIN MATERIALS

[75] Inventors: Zhenyu Yang, Old Saybrook; Weitao Jia, Wallingford, both of Conn.

[73] Assignee: Jeneric Pentron Incorporated, Wallingford, Conn.

[21] Appl. No.: 08/998,849

[22] Filed: Dec. 29, 1997

Related U.S. Application Data

[60] Provisional application No. 60/036,184, Jan. 17, 1997.
[51] Int. Cl.$^6$ .............................. A61K 6/083; C08F 18/24
[52] U.S. Cl. .......................... 523/116; 523/115; 523/117; 524/558; 524/559; 524/443; 526/301; 526/314
[58] Field of Search ..................................... 523/115, 116, 523/117; 524/558, 559, 443; 526/301, 314

[56] References Cited

U.S. PATENT DOCUMENTS

| | | |
|---|---|---|
| 3,200,142 | 8/1965 | Bowen . |
| 3,815,239 | 6/1974 | Lee, Jr. et al. . |
| 4,302,381 | 11/1981 | Omura et al. . |
| 4,479,782 | 10/1984 | Orlowski et al. . |
| 4,581,389 | 4/1986 | Schaefer . |
| 4,588,756 | 5/1986 | Bowen . |
| 4,762,863 | 8/1988 | Sasaki et al. ............................ 523/116 |
| 5,182,332 | 1/1993 | Yamamoto et al. .................... 523/116 |
| 5,276,068 | 1/1994 | Waknine ................................. 523/116 |

FOREIGN PATENT DOCUMENTS

| | | |
|---|---|---|
| 1428454 | 3/1976 | United Kingdom . |
| 2079297 | 1/1982 | United Kingdom ................... 523/116 |

*Primary Examiner*—Andrew E. C. Merriam
*Attorney, Agent, or Firm*—Cantor Colburn LLP

[57] ABSTRACT

A dental resin composition is presented, comprising an ethoxylated bisphenol A dimethacrylate having the formula $$CH_2=C(CH_3)CO_2(C_2H_4O)_xC_6H_4C(CH_3)_2$$
$$C_6H_4(OC_2H_4)_yO_2CC(CH_3)=CH_2$$

wherein x+y is an integer from 1 to 20, and preferably from 2 to 7, together with a methacrylate oligomer and an optional diluent monomer. The composition is suitable for use for dental fillers adhesives, and the like, and has improved water sorption and excellent wear resistance.

34 Claims, No Drawings

DENTAL RESIN MATERIALS

CROSS-REFERENCE TO RELATED APPLICATIONS

This application claims priority to U.S. Provisional Application Ser. No. 60/036,184, filed Jan. 17, 1997.

BACKGROUND OF THE INVENTION

1. Field of the Invention

This invention relates to polymeric condensation products for restorative dentistry. More particularly, it relates to polymeric condensation products useful as a component of filled resin composites. Depending on filler content, such filled resin composites may be used as crown and bridge materials, either with or without an alloy substrate; or as reconstructive materials, bioprostheses, restorative materials, filling materials, inlays, onlays, laminate veneers, and the like. The polymeric condensation products of the present invention have improved water sorption characteristics and excellent wear resistance.

2. Brief Description of the Related Art

In recent years, materials used for dental restorations have comprised principally acrylate or methacrylate polymers. Typical acrylate resinous materials are disclosed in U.S. Pat. No. 3,066,112 to Bowen, U.S. Pat. No. 3,179,623 to Bowen, U.S. Pat. No. 3,194,784 to Bowen, U.S. Pat. No. 3,751,399 to Lee et al. and U.S. Pat. No. 3,926,906 to Lee et al. An especially important methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA"). Polyurethane dimethacrylates (hereinafter abbreviated to PUDMA) are also commonly-used principal polymers in dental restorative materials of this type.

Since BIS-GMA is highly viscous at room temperature, it is generally diluted with an acrylate or methacrylate monomer having a lower viscosity such as trimethylol propyl trimethacrylate, 1,6-hexanediol dimethacrylate, 1,3-butanediol dimethacrylate, and the like. Other dimethacrylate monomers, such as ethylene glycol dimethacrylate, diethylene glycol dimethacrylate, triethylene glycol dimethacrylate and tetraethylene glycol dimethacrylate, are also in general use as diluents.

When these acrylic resinous materials were first developed, they were used for dental restorative purposes unfilled, that is, without the presence of any other organic or inorganic component. However, because acrylic materials exhibit high coefficients of thermal expansion relative to the coefficient of thermal expansion for the tooth structure, these unfilled substances proved to be less than satisfactory. The disparity in thermal expansion, coupled with high shrinkage upon polymerization, resulted in poor marginal adaptability and ultimately led to secondary decay. Furthermore, the wear and abrasion characteristics and the overall physical, mechanical and optical properties of these unfilled acrylic resinous materials were quite poor. Composite dental restorative materials containing methacrylate resins and fillers were thus developed, the fillers generally comprising inorganic materials based on silica, silicate glass, or quartz.

There are now available materials which exhibit high diametral tensile strength, excellent optical properties and polishability, and low water sorption while at the same time complying with all of the requirements specified in ADA Specification No. 27 for Direct Filling Resins. Particularly suitable restorative materials include the compositions having improved inorganic filler materials such as those disclosed in commonly assigned U.S. Pat. No. 4,547,531 to Waknine, disclosing self-curing two-component compositions, and U.S. Pat. No. 4,544,359 to Waknine, disclosing visible light curable compositions.

Other monomers and polymers particularly suited for dental restorative resins and other dental applications are disclosed in commonly assigned U.S. Pat. No. 5,276,068 to Waknine and U.S. Pat. No. 5,444,104 to Waknine. Such materials make use of a novel polycarbonate dimethacrylate which is the condensation product of two parts of hydroxyalkylmethacrylate of the formula $H_2C=C(CH_3)C(O)O-A-OH$, in which A is a $C_1-C_6$ alkylene, and 1 part of a bis(chloroformate) of the formula $ClC(O)-(OR)_n-OC(O)Cl$, in which R is a $C_2-C_5$ alkylene having at least two carbon atoms in its principal chain, and n is an integer in the range from 1 to 4. Where no diluent monomer is used, this novel polycarbonate dimethacrylate is reacted in an amount of about 65–75% by weight of the total resin composition with a secondary monomer in an amount of about 25–35% by weight of the total resin composition. Suitable secondary monomers include BIS-GMA, PUDMA, and the like. Alternatively, where a diluent monomer is used, the novel polycarbonate dimethacrylate is present in an amount of about 30–80%, with 5–60% of a secondary monomer and 1–50% of a diluent monomer. This polycarbonate dimethacrylate imparts excellent strength to the cured resin, but it is somewhat costly.

Thus, despite recent advances in the development of filled dental restorative materials having led to composites having higher resistance to abrasion, better handling characteristics, and more satisfactory visual appearance, there remains a need for improvement in the wear resistance of filled compositions used as crown and bridge materials and denture-base materials. Improved water sorption in particular would contribute to the long-term stability of a restoration and is particularly desirable.

SUMMARY OF THE INVENTION

The drawbacks and deficiencies of the prior art are remedied by the resinous dental compositions in accordance with the present invention, wherein the resinous dental composition is derived from the reaction of an ethoxylated bisphenol A dimethacrylate and a co-monomer, preferably a polycarbonate dimethacrylate condensation product described in U.S. Pat. Nos. 5,276,068 and 5,444,104 to Waknine. The resinous dental composition can additionally include a third, diluent monomer to increase the surface wettability of the resinous matrix.

The ethoxylated bisphenol A dimethacrylate in accordance with the present invention has the following structure:

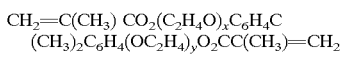

wherein x+y is an integer from 1 to 20, and preferably an integer from 2 to 7.

The preferred polycarbonate dimethacrylate condensation product co-monomer results from the condensation, under carefully controlled conditions, of two parts by weight of a hydroxyalkylmethacrylate of the formula $H_2C=C(CH_3)C(O)O-A-OH$, in which A is a $C_1-C_6$ alkylene, with 1 part by weight of a bis(chloroformate) of the formula $ClC(O)-(OR)_n-OC(O)Cl$, in which R is a $C_2-C_5$ alkylene having at least two carbon atoms in its principal chain, and n is an integer in the range from 1 to 4.

In one embodiment of the present invention there is provided filled compositions comprising the ethoxylated bisphenol A dimethacrylate, together with the above-described polycarbonate dimethacrylate condensation products and various inorganic additives and/or fillers. In an important feature of the invention, the amount of the co-monomer polycarbonate dimethacrylate is minimized, leading to improved water sorption properties, while maintaining exceptionally good wear resistance. Such filled compositions are useful for a variety of dental treatments and restorative functions including crown and bridge materials, luting agents or cement denture-base materials, orthodontic materials and sealants, and dental restorative materials.

The dental compositions of this invention include visible light curable, self-curing, dual curing, and vacuum, heat, and pressure curable compositions as well as any combination thereof The visible light curable compositions include, in addition to the ethoxylated bisphenol A dimethacrylate and the second co-monomeric component, the usual polymerization initiators, polymerization accelerators, ultraviolet absorbers, fluorescent whitening agents, and the like. In the self-curing compositions, the polymerization accelerator can be included in the resinous composition which is used for pretreating the exposed dentin. The heat and pressure curable compositions, which are generally filled compositions, include, in addition to the monomeric components, a heat cure initiator such as benzoyl peroxide, 1,1'-azobis (cyclohexanecarbonitrile), or other free radical initiators.

DETAILED DESCRIPTION OF THE INVENTION

The present invention comprises a dental resin composition comprising an ethoxylated bisphenol A dimethacrylate and a co-monomer, preferably a dimethacrylate oligomer. In an important feature of the present invention, use of an ethoxylated bisphenol A dimethacrylate allows the relative amounts of dimethacrylate oligomer to be decreased in comparison to other resin formulations, for example those disclosed in U.S. Pat. Nos. 5,276,068 and 5,444,104 to Waknine. Use of the ethoxylated monomer unexpectedly improves the wettability of the cured resin composition, thereby resulting in better filler incorporation. The cured resins thus obtained have improved water sorption characteristics, improved stain resistance, and further possess excellent wearability.

The ethoxylated bisphenol A dimethacrylate in accordance with the present invention has the structure

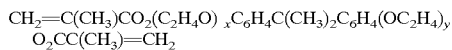
$CH_2=C(CH_3)CO_2(C_2H_4O)_xC_6H_4C(CH_3)_2C_6H_4(OC_2H_4)_y$
$O_2CC(CH_3)=CH_2$ wherein x+y is an integer from 1 to 20, and preferably from 2 to 7. Such material is available from Sartomer®, under the trade name SR348 or SR480, or from Esstech. SR480 provides a material wherein x+y is 10. Esstech provides a material wherein x+y is an integer from 5 to 7.

The preferred dimethacrylate oligomer for use with the ethoxylated bisphenol A dimethacrylate of the present invention is a polycarbonate dimethacrylate condensation product obtained by the condensation reaction of a hydroxy alkyl methacrylate of the general formula $H_2CC(CH_3)C(O)O—A—OH$, in which A is a $C_1–C_6$ alkylene, with 1 part of a bis(chloroformate) of the formula $ClC(O)—(OR)_n—OC(O)Cl$, in which R is a $C_2–C_5$ alkylene having at least two carbon atoms in its principal chain, and n is an integer from 1 to 4. By "principal chain" is meant the chain of carbon atoms serving as a bridge between the oxygen atoms. Such preferred polycarbonate dimethacrylate condensation products have been described in commonly assigned U.S. Pat. No. 5,276,068, and U.S. Pat. No. 5,444,104, the disclosure of both of which is herein incorporated by reference. A particularly preferred polycarbonate dimethacrylate is the condensation product of 2-hydroxyethylmethacrylate (2-HEMA) and triethylene glycol bis(chloroformate).

In an important feature of the present invention, use of the ethoxylated bisphenol A dimethacrylate allows the relative amounts of dimethacrylate oligomer to be decreased in comparison to other resin formulations, for example those disclosed in U.S. Pat. Nos. 5,276,068 and 5,444,104. Use of the ethoxylated bisphenol A dimethacrylate, in combination with the decreased quantity of methacrylate oligomer, results in a resin having improved water sorption characteristics. The material further has excellent wearability.

While the above polycarbonate dimethacrylate condensation products are preferred, other acrylic resinous materials are suitable for use in accordance with the present invention. Such materials include, but are not limited to, urethane dimethacrylate (UDMA), diurethane dimethacrylate (DUDMA), and other monomers and oligomers known in the art.

In addition to the two aforementioned monomeric components, the resinous dental compositions of the present invention can further include a diluent monomer to increase the surface wettability of the composition by decreasing the viscosity of the polymerization medium. Suitable diluents include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol) dimethacrylate and tetra(ethylene glycol) dimethacrylate; diisocyanates, such as 1,6-hexamethylene diisocyanate and ethoxylated monomers such as 1,6-hexanedioldimethacrylate. Tri(ethylene glycol) dimethacrylate (TEGDMA) is particularly preferred.

In accordance with an important feature of the present invention, the ethoxylated bisphenol A dimethacrylate is used in an amount in the range from 65 to about 90 percent by weight of the total resin composition. Preferably, the ethoxylated bisphenol A dimethacrylate is used in an amount in the range from about 70 to about 80 percent by weight of the total resin composition. Typically, the dimethacrylate oligomer, preferably the above-described polycarbonate dimethacrylates, is incorporated into the resinous composition in an amount from about 10 to about 30 weight percent of the total resin composition. The optional diluent monomer is typically present in an amount from about 0 to about 40 weight percent of the total resin composition.

When no diluent component is employed the preferred range for the ethoxylated bisphenol A dimethacrylates is from 65 to about 90 weight percent, and most preferably about 70 weight percent of the total resin composition, and the preferred range for the dimethacrylate oligomer is from about 10 to about 30 weight percent, and most preferably about 30 weight percent of the total resin composition.

In addition to the above materials, the resinous compositions of this invention can also typically include polymerization initiators, polymerization accelerators, ultra-violet light absorbers, anti-oxidants, and other additives well known in the art.

The polymerization initiators suitable in the resinous adhesives of this invention are conventional initiators known in the art. For example, visible light curable compositions employ light-sensitive compounds such as betzil diketones, and in particular, DL-camphorquinone in amounts ranging from about 0.05 to 0.5 weight percent. Self-curing compositions will generally contain free radical polymerization initiators such as, for example, a peroxide in amounts ranging from about 2 to 6 weight percent. Particularly suitable free radical initiators are lauryl peroxide, tributyl hydroperoxide and, more particularly benzoyl peroxide, The polymerization accelerators suitable for use in the compositions of this invention are the various organic tertiary amines well known in the art. In visible light curable compositions, the tertiary amines are generally acrylate derivatives such as dimethylaminoethyl methacrylate and, particularly, diethylaminoethyl methacrylate in amounts ranging from about 0.05 to 0.5 weight percent. In the self-curing compositions, the tertiary amines are generally aromatic tertiary amines, such as dimethyl-p-toluidine, dihydroxyethyl-p-toluidine and the like, in amounts ranging from about 0.05 to about 4.0 weight percent.

It is furthermore preferred to employ an ultraviolet absorber in these resinous adhesives in amounts ranging from about 0.05 to about 5.0 weight percent. Such UV absorbers are particularly desirable in the visible light curable compositions in order to avoid discoloration of the resin from any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y.

Typical visible light curable resinous dental compositions according to this invention comprise:

(a) 10–30 weight percent of the polycarbonate dimethacrylate condensation product of triethylene glycol bis(chloroformate) and 2-hydroxyethylmethacrylate;

(b) 65–90 weight percent of the ethoxylated bisphenol A dimethacrylate in accordance with the present invention;

(c) 0.05–0.50 weight percent of DL-camphorquinone;

(d) 0.05–0.5 weight percent of diethylamino ethyl methacrylate; and (e) 0.05–5 weight percent of TINUVIN P ultraviolet absorber in specific amounts within these ranges to yield a 100% by weight polymerization system. A particularly preferred embodiment comprises 67.69% by weight ethoxylated bisphenol A dimethacrylate, 29.704% by weight of the polycarbonate dimethacrylate condensation product of triethylene glycol bis(chloroformate) and 2-hydroxyethylmethacrylate, 0.072% by weight 2-(2-hydroxy-5-tert-octylphenyl)bezotriazole, 0.019% by weight 2,5-bis (5-tert-butyl-2-benzoxazoyl)thiophene, 0.193% by weight camphorquinone, 0.097% by weight benzil, 0.967% by weight 2,4,6-trimethyl benzoyldiphenylphosphine oxide, 0.048% by weight butylhydroxytoluene, 0.242% by weight diethylaminoethyl methacrylate, and 0.967% by weight 1,1'-azobis(cyanocyclohexane).

In one preferred embodiment of the present invention, the resinous dental composition further comprises a diluent monomer, such as tri(ethylene glycol) dimethacrylate (TEGDMA). In a visible light curable composition including TEGDMA, the resulting overall compositions in weight percent comprise:

| Broad Range | Preferred Range | Most Preferred | Component |
| --- | --- | --- | --- |
| 1–30 | 5–20 | 10 | Polycarbonate dimethacrylate condensation product of triethylene glycol bis(chloroformate) and 2-HEMA |
| 65–90 | 70–80 | 70 | Ethoxylated bisphenol A dimethacrylate |
| 0–40 | 10–30 | 20 | TEGDMA |
| 0.05–0.40 | 0.200–0.300 | 0.25 | diethylaminoethylmethacrylate |
| 0.25–4.0 | 0.500–1.500 | 1.0 | TINUVIN P (ultra-violet absorber) |
| 0.05–0.50 | 0.10–0.30 | 0.25 | 2,3-d-bornanedione or DL-camphoroquinone |
| .001–.2500 | 0.00–0.20 | 0.05 | BHT |
| 0.00–0.500 | 0.00–0.2500 | 0.0097 | Fluorescent/whitening agent (UNITEX OB) | in specific amounts within these ranges to yield a 100% by weight polymerization system.

A diluent, such as TEGDMA, is also preferably employed in the self-cure and dual-cure resinous dental compositions in an amount of up to about 40 weight percent.

In addition to unfilled compositions, the dental compositions of the present invention can also be filled or partially filled. The filled compositions of the invention can include all of the inorganic fillers currently used in dental restorative materials, the amount of such filler being determined by the specific function of the filled materials. Thus, for example, where crown and bridge materials are being prepared, the resinous compositions of the present invention are present in amounts ranging from about 10 to about 40 weight percent of the total composition, and the filler materials are present in amounts ranging from about 60 to about 90 weight percent of the total composition. Typical compositions for crown and bridge materials are about 25% by weight of the resinous material and about 75% by weight of the filler.

The filled compositions of this invention can, in general, include any suitable filler which is capable of being covalently bonded to the resin matrix itself or to a coupling agent which is covalently bonded to both. Examples of suitable filling materials include but are not limited to, silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania. Particularly suitable fillers for dental restorative materials prepared in accordance with this invention are those having a particle size ranging from about 0.1–5.0 μm with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in U.S. Pat. No. 4,544,359 and U.S. Pat. No. 4,547,531, pertinent portions of which are incorporated herein by reference. One consideration in the selection of a filler is the difference in the index of refraction of the filler material and that of the resinous matrix. In general, a more aesthetically pleasing restoration can be obtained when the difference between the index of refraction of the filler material and that of the resin matrix is small.

As with the unfilled compositions, the filled and partially filled compositions can be prepared in visible light curable formulations, self-curing, and dual curing formulations. In addition, the filled compositions can be prepared in heat pressure curing formulations. It has surprisingly been found that heat-pressure curing the filled or partially filled dental compositions of the present invention results in a material which exhibits superior physical and mechanical properties when compared to other modes of cure. The filled composite restorative materials can be prepared by admixing from about 20 to 30% by weight, preferably 20–26% by weight, of the unfilled visible light curable self-curing, dual-curing or heat-pressure curable composition dental composition with from about 65 to about 85% by weight, preferably about 75 to 83% by weight of inorganic filler material.

The composite dental restorative material of the present invention preferably comprises an inorganic filler having an average particle size diameter of from about 0.5 to 5 microns homogeneously dispersed in an organic polymerizable monomeric matrix comprising the ethoxylated dimethacrylate. In addition, a relatively small amount of fumed silica is also predispersed within the monomeric matrix. The inorganic filler primarily comprises an X-ray opaque alkali metal or alkaline earth metal silicate such as lithium alumina silicate, barium silicate, strontium silicate, barium borosilicate, strontium borosilicate, borosilicate, as well as any of the aforementioned materials. For purposes of illustration, and as the preferred silicate species, barium borosilicate will hereinafter be employed as being typical of the alkali metal or alkaline earth metal silicates which can be suitably employed in the present invention. The barium borosilicate exhibits an index of refraction close to that of the organic monomeric matrix in which it is dispersed. The filler can additionally contain a relatively small amount of diameter of from about 0.5 to about 5 microns, can be found in the aforementioned U.S. Pat. No. 4,544,539 and U.S. Pat. No. 4,547,531.

This invention is further illustrated by reference to the following examples, which are included for illustrative purposes only and are not to be construed in limitation of the claims.

EXAMPLES

The abbreviations and source for each component of the resins prepared in the Examples are as follows:

| Abbreviation | Component | Source |
|---|---|---|
| E | Ethoxylated bisphenol A dimethacrylate (Esstech) | Esstech |
| T | Tri(ethylene glycol)dimethacrylate | Esstech |
| P | polycarbonate condensation product of triethylene glycol bis(chloroformate) and 2-HEMA | Esstech |
| B | Bis-GMA | Esstech |

The Table below shows comparative data for the resin compositions in accordance with the present invention and the prior art. All amounts are given in weight percent. About 77–82 weight percent of conventional particulate filler mixture was used, together with conventional curing agents as discussed above. Samples were generally cured by VLC using a Cute Lite Plus available from Jeneric/Pentron, Inc. and heat and vacuum cure using a vacuum Conquest Curing Oven, also available from Jeneric/Pentron, Inc. MOR (a measure of flexural strength) and diametral tensile compression strength (DTS) were measured on a Universal Instron machine. Water sorption (microgram per cubic millimeter) was measured in accordance with ADA Specification No. 27 for Direct Filling Resins.

| Resin | | | | | Water Sorption ($\mu$g/mm$^3$) One Week | Water Sorption ($\mu$g/mm$^3$) One Month | Volume Polymerization Shrinkage (%) | Linear Polyermization Shrinkage (%) |
|---|---|---|---|---|---|---|---|---|
| E | P | T | MOR(psi) | DTS(psi) | | | | |
| 80 | 20 | — | — | 8180(1077) | 14.4 | 16.4 | — | — |
| 60 | 20* | 20 | — | 8981(342) | 14.1 | 15.2 | — | — |
| 60 | 20 | 20 | 16000(806) | 8397(971) | 13.3 | 13.9 | — | — |
| 60 | 20 | 20 | 14369(874) | 8102(598) | 17.2 | 20.1 | 2.14 | 0.5 |
| 70 | 10 | 20 | 20442(1560) | — | 7.84 | 9.74 | — | — |
| 70 | 10 | 20 | 20369(1011) | 8664(550) | 7.84 | 11.8 | 1.14 | 0.4 |
| 70 | 10 | 20 | 16010(1152) | — | 12.4 | 14.7 | — | — |
| 70 | 10 | 20 | 19000(1999) | 9570(547) | 11.4 | — | 0.86 | — |
| 70 | 10 | 20 | 19094(1983) | — | 9.08 | 10.2 | 1.91 | — |
| 70 | 30 | — | 21319(1780) | — | 9.34 | 11.4 | 1.23 | — |
| 70 | 30 | — | 20656(2000) | 8504(630) | 12.3 | 14.9 | 2.61 | |
| 70 | 30 | — | 20263(2322) | — | 7.46 | — | — | — |
| 70 | 30 | — | 19546(2112) | 8587(660) | 8.45 | 11.6 | 1.9 | 0.4 |

*UDMA in place of P borosilicate glass which imparts greater compressive strength to the resulting composite and enhances the translucency thereof thereby enabling better blending of the restorative material with the adjacent teeth. In addition, the presence of the borosilicate glass helps narrow the gap in the mismatch of refractive indices between the barium borosilicate inorganic fiber phase and the organic monomeric matrix.

Details of the preparation of the inorganic filler, which comprises a mixture of from about 5 to about 20% by weight of borosilicate glass and from about 80 to about 95% by weight barium borosilicate, and has an average particle size Despite some variablity in the data, in general, the data indicate that resins in accordance with the present invention have good flexural and tensile diametral strength, acceptable shrinkage characteristics, and superior water sorption characteristics. They also have exceptionally good wear resistance. Variation in the identity of the curing agents and/or the filler had minor effect (data not shown).

The data in the Table below demonstrate that the advantageous water sorption characteristic results in dental materials that stain significantly less than prior art dental materials.

| Sample No. | Resin E | P | B | T | Flexural Strength(psi) | Water Sorption (1 week) | Coffee Stain Resistance (1 week) |
|---|---|---|---|---|---|---|---|
| 1 | 70 | 30 | — | — | 20263(2322) | 7.46 | no significant change |
| 2* | — | 30 | 70 | — | 17167(1549) | 15.7 | significantly darkened |
| 3* | 70 | 30 | — | — | 16028(1958) | 12.2 | significantly darkened |
| 4* | — | 50 | 20 | 30 | 16706(848) | 19.3 | significantly darkened |

*prior art formulation

In particular, direct comparison of Sample 1 in accordance with the present invention with Samples 2, 3, and 4 in accordance with U.S. Pat. Nos. 5,276,068 and 5,444,104 to Waknine demonstrates the superior water sorption for the composites using an ethoxylated bisphenol A dimethacrylate wherein x+y=20 preferably, x+y is an integer from 5 to 7. Superior water sorption characteristics are expected to result in less staining, and in fact, when tested for coffee stain resistance, Sample 1 showed no significant change in coloration, whereas Samples 2, 3, and 4 darkened significantly over one week. Poor wettability for fillers was also noted for Samples 2, 3, and 4, as well as much lower strength characteristics.

What is claimed is:

1. A curable dental resin composition comprising
   (a) from about 10 to about 30 weight percent of a methacrylate oligomer;
   (b) from 65 to about 90 weight percent of an ethoxylated bisphenol A dimethacrylate having the formula

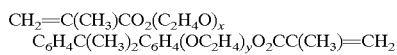

wherein x+y is 10; and
   (c) from about 0 to about 40 weight percent of a diluent monomer for decreasing the viscosity of the dental resin composition, wherein each of the components (a), (b), and (c) is a different monomer and such that the specific amounts with the ranges yield a 100% by weight polymerization system.

2. The curable dental resin composition of claim 1, wherein
   the methacrylate oligomer is a urethane dimethacrylate, diurethane dimethacrylate, or the condensation product of two parts of hydroxyalkylmethacrylate of the formula $H_2C\!=\!C(CH_3)C(O)O$—A—OH, in which A is a $C_1$–$C_6$ alkylene, and 1 part of a bis(chloroformate) of the formula $ClC(O)$—$(OR)_n$—$OC(O)Cl$, in which R is a $C_2$–$C_5$ alkylene having at least two carbon atoms in its principal chain, and n is an integer from 1 to 4, or a mixture thereof.

3. A curable dental resin composition comprising:
   (a) from 10 to about 30 weight percent of a methacrylate oligomer comprising the condensation product of triethylene glycol bis(chloroformate) and 2-hydroxyethylmethacrylate;
   (b) from 65 to about 90 weight percent of an ethoxvlated bisphenol A dimethacrylate having the formula

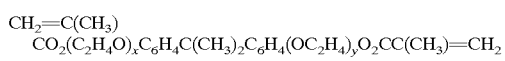

wherein x+y is an integer from 1 to 20; and
   (c) from about 0 to about 40 weight percent of a diluent monomer for decreasing the viscosity of the dental resin composition, wherein each of the components (a), (b), and (c) is a different monomer and such that the specific amounts with the ranges yield a 100% by weight polymerization system.

4. The curable dental resin composition of claim 1, wherein
   the diluent monomer is a hydroxy alkyl methacrylate, ethylene glycol methacrylate, diisocyanate, ethoxylated monomer, or a combination thereof.

5. The curable dental resin composition of claim 4, wherein
   the diluent monomer is 2-hydroxyethyl methacrylate, 2-hydroxypropyl methacrylate, ethylene glycol methacrylate, diethylene glycol methacrylate, tri(ethylene glycol) dimethacrylate, tetra(ethylene glycol) dimethacrylate, 1,6-hexanedioldimethacrylate, or a combination thereof.

6. The curable dental resin composition of claim 5, wherein
   the diluent monomer is tri(ethylene glycol) dimethacrylate.

7. The curable dental resin composition of claim 1, further comprising
   inorganic filler.

8. The curable dental resin composition of claim 7, wherein
   the inorganic filler is a silica, silicate glass, quartz, barium borosilicate, strontium silicate, barium silicate, strontium borosilicate, borosilicate, lithium silicate, amorphous silica, calcium phosphate, alumina, zirconia, tin oxide, titania, or a combination thereof.

9. The curable dental resin composition of claim 1, wherein
   the methacrylate oligomer is present in an amount from about 10 to about 20 weight percent, the ethoxylated bisphenol A dimethacrylate is present in an amount from about 70 to about 80 weight percent, and the diluent monomer is present in an mount from about 10 to about 30 weight percent.

10. The curable dental resin composition of claim 9, wherein
    the methacrylate oligomer is present in an amount of about 10 weight percent, the ethoxylated bisphenol A dimethacrylate is present in an amount of about 70 weight percent, and the diluent monomer is present in an amount of about 20 weight percent.

11. The dental resin composition of claim 1, wherein
    the methacrylate oligomer is present in an amount of about 30 weight percent, and the ethoxylated bisphenol A dimethacrylate is present in an amount of about 68 weight percent.

12. A dental restoration comprising a material formed by curing a composition comprising:
    (a) from about 10 to about 30 weight percent of a methacrylate oligomer;

(b) from 65 to about 90 weight percent of an ethoxylated bisphenol A dimethacrylate having the formula

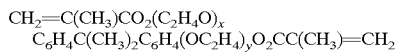

wherein x+y is 10; and (c) from about 0 to about 40 weight percent of a diluent monomer for decreasing the viscosity of the dental resin composition, wherein each of the components (a), (b), and (c) is a different monomer and such that the specific amounts with the ranges yield a 100% by weight polymerization system.

13. The dental restoration of claim 12, wherein
the methacrylate oligomer is a urethane dimethacrylate, diurethane dimethacrylate, or the condensation product of two parts of hydroxyalkylmethacrylate of the formula $H_2C=C(CH_3)C(O)O-A-OH$, in which A is a $C_1-C_6$ alkylene, and 1 part of a bis(chloroformate) of the formula $ClC(O)-(OR)_n-OC(O)Cl$, in which R is a $C_2-C_5$ alkylene having at least two carbon atoms in its principal chain, and n is an integer from 1 to 4, or a mixture thereof.

14. A dental restoration comprising a material formed by curing a composition comprising:

(a) from about 10 to about 30 weight percent of a methacrylate oligomer comprising the condensation product of triethylene glycol bis(chloroformate) and 2-hydroxyethylmethacrylate;

(b) from about 65 to about 90 weight percent of an ethoxylated bisphenol A dimethacrylate having the formula

wherein x+y is an integer from 1 to 20; and (c) from about 0 to about 40 weight percent of a diluent monomer for decreasing the viscosity of the dental resin composition, wherein each of the components (a), (b), and (c) is a different monomer and such that the specific amounts with the ranges yield a 100% by weight polymerization system.

15. The dental restoration of claim 12, wherein
the diluent monomer is a hydroxy alkyl methacrylate, ethylene glycol methacrylate, diisocyanate, ethoxylated monomer, or a combination thereof.

16. The dental restoration of claim 15, wherein
the diluent monomer is 2-hydroxyethyl methacrylate, 2-hydroxypropyl methacrylate, ethylene glycol methacrylate, diethylene glycol methacrylate, tri(ethylene glycol) dimethacrylate, tetra(ethylene glycol) dimethacrylate, 1,6-hexanedioldimethacrylate, or a combination thereof.

17. The dental restoration of claim 16, wherein
the diluent monomer is tri(ethylene glycol) dimethacrylate.

18. The dental restoration of claim 12, further comprising inorganic filler.

19. The dental restoration of claim 18, wherein
the inorganic filler is a silica, silicate glass, quartz, barium borosilicate, strontium silicate, barium silicate, strontium borosilicate, borosilicate, lithium silicate, amorphous silica, calcium phosphate, alumina, zirconia, tin oxide, titania, or a combination thereof.

20. The dental restoration of claim 12, wherein
the methacrylate oligomer is present in an amount from about 10 to about 20 weight percent, the ethoxylated bisphenol A dimethacrylate is present in an amount from about 70 to about 80 weight percent, and the diluent monomer is present in an amount from about 10 to about 30 weight percent.

21. The dental restoration of claim 12, wherein
the methacrylate oligomer is present in an amount of about 10 weight percent, the ethoxylated bisphenol A dimethacrylate is present in an amount of about 70 weight percent, and the diluent monomer is present in an amount of about 20 weight percent.

22. The dental restoration of claim 12, wherein
the methacrylate oligomer is present in an amount of about 30 weight percent, and the ethoxylated bisphenol A dimethacrylate is present in an amount of about 68 weight percent.

23. The curable dental resin composition of claim 3, wherein
x+y is an integer from 5 to 7.

24. The curable dental resin composition of claim 3, wherein
the diluent monomer is selected from the group consisting of hydroxy alkyl methacrylates, ethylene glycol methacrylates, ethoxylated monomers, 2-hydroxyethyl methacrylate, 2-hydroxypropyl methacrylate, ethylene glycol methacrylate, diethylene glycol methacrylate, tri(ethylene glycol) dimethacrylate, tetra(ethylene glycol) dimethacrylate, 1,6-hexanedioldimethacrylate, or a combination thereof.

25. The curable dental resin composition of claim 3, further comprising inorganic filler.

26. The curable dental resin composition of claim 25, wherein
the inorganic filler is a silica, silicate glass, quartz, barium borosilicate, strontium silicate, barium silicate, strontium borosilicate, borosilicate, lithium silicate, amorphous silica, calcium phosphate, alumina, zirconia, tin oxide, titania, or a combination thereof.

27. The curable dental resin composition of claim 3, wherein
the methacrylate oligomer is present in an amount from about 10 to about 20 weight percent, the ethoxylated bisphenol A dimethacrylate is present in an amount from about 70 to about 80 weight percent, and the diluent monomer is present in an amount from about 10 to about 30 weight percent.

28. The curable dental resin composition of claim 3, wherein
the methacrylate oligomer is present in an amount of about 10 weight percent, the ethoxylated bisphenol A dimethacrylate is present in an amount of about 70 weight percent, and the diluent monomer is present in an mount of about 20 weight percent.

29. The curable dental resin composition of claim 14, wherein
x+y is an integer from 5 to 7.

30. The curable dental resin composition of claim 14, wherein
the diluent monomer is selected from the group consisting of hydroxy alkyl methacrylates, ethylene glycol methacrylates, ethoxylated monomers, 2-hydroxyethyl methacrylate, 2-hydroxypropyl meihacrylate, ethylene glycol methacrylate, diethylene glycol methacrylate, tri(ethylene glycol) dimethacrylate, tetra(ethylene glycol) dimethacrylate, 1,6-hexanedioldimethacrylate, or a combination thereof.

31. The curable dental resin composition of claim 14, further comprising inorganic filler.

32. The curable dental resin composition of claim 31, wherein the inorganic filler is a silica, silicate glass, quartz, barium borosilicate, strontium silicate, barium silicate, strontium borosilicate, borosilicate, lithium silicate, amorphous silica, calcium phosphate, alumina, zirconia, tin oxide, titania, or a combination thereof.

33. The curable dental resin composition of claim 14, wherein the methacrylate oligomer is present in an amount from about 10 to about 20 weight percent, the ethoxylated bisphenol A dimethacrylate is present in an amount from about 70 to about 80 weight percent, and the diluent monomer is present in an amount from about 10 to about 30 weight percent.

34. The curable dental resin composition of claim 14, wherein the methacrylate oligomer is present in an amount of about 10 weight percent, the ethoxylated bisphenol A dimethacrylate is present in an amount of about 70 weight percent, and the diluent monomer is present in an mount of about 20 weight percent.

* * * * *

UNITED STATES PATENT AND TRADEMARK OFFICE
CERTIFICATE OF CORRECTION

PATENT NO. : 5,969,000
DATED : October 19, 1999
INVENTOR(S) : Zhenyu Yang et al.

It is certified that error appears in the above-identified patent and that said Letters Patent is hereby corrected as shown below:

Column 3,
Line 17, after "thereof", insert a period -- . --.

Column 12,
Line 63, deleted "meihacrylate" and insert therefor -- methacrylate --.

Signed and Sealed this

Tenth Day of September, 2002

Attest:

Attesting Officer

JAMES E. ROGAN
Director of the United States Patent and Trademark Office